(12) United States Patent
Zhang

(10) Patent No.: US 9,060,928 B2
(45) Date of Patent: Jun. 23, 2015

(54) TACROLIMUS INJECTION PREPARATION

(75) Inventor: Na Zhang, Fuzhou (CN)

(73) Assignee: FUZHOU HARVESTER PHARMACEUTICAL R&D CO., LTD., Fujian (CN)

( * ) Notice: Subject to any disclaimer, the term of this patent is extended or adjusted under 35 U.S.C. 154(b) by 418 days.

(21) Appl. No.: 13/255,127

(22) PCT Filed: Apr. 2, 2010

(86) PCT No.: PCT/CN2010/070519
§ 371 (c)(1),
(2), (4) Date: Sep. 7, 2011

(87) PCT Pub. No.: WO2010/121503
PCT Pub. Date: Oct. 28, 2010

(65) Prior Publication Data
US 2012/0059027 A1    Mar. 8, 2012

(30) Foreign Application Priority Data

Apr. 24, 2009 (CN) .......................... 2009 1 0111552

(51) Int. Cl.
*A61K 31/436* (2006.01)
*A61P 37/06* (2006.01)
*A61K 9/00* (2006.01)
*A61K 47/44* (2006.01)

(52) U.S. Cl.
CPC ............... *A61K 9/0019* (2013.01); *A61K 47/44* (2013.01)

(58) Field of Classification Search
None
See application file for complete search history.

(56) References Cited

U.S. PATENT DOCUMENTS 5,260,301 A * 11/1993 Nakanishi et al. ............ 514/291

FOREIGN PATENT DOCUMENTS

| CN | 101056616 | 10/2007 |
|----|-----------|---------|
| KR | 0177158   | 3/1999  |
| KR | 0206722   | 7/1999  |
| KR | 20010006070 | 1/2001 |

OTHER PUBLICATIONS

Chung et al. In Arch Pharm Res 27(8) 878-883 (2004).*
Cremophor EL in www.chemicalbook/ProductChemicalPropertiesCB075518_EN.htm (retrieved from the internet Jun. 5, 2013).*
Kolliphor EL in en.wikipedia.org/wiki/Kolliphor_EL (retrieved from the internet Jun. 5, 2013).*
PROGRAF Labelling Information 2012 (retrieved from the interenet Aug. 4, 2013).*

* cited by examiner

*Primary Examiner* — Dennis Heyer
(74) *Attorney, Agent, or Firm* — Lihua Zheng; Proskauer Rose LLP

(57) ABSTRACT

A tacrolimus injection preparation comprising tacrolimus, polyoxyethylene castor oil (35), and non-aqueous solvent is disclosed. Preferably the weight ratio of polyoxyethylene castor oil (35) to tacrolimus in the injection preparation is 10-20:1. The injection preparation significantly decreased the clinical risk.

3 Claims, No Drawings

TACROLIMUS INJECTION PREPARATION

RELATED APPLICATIONS

This application is U.S. National Phase Application of PCT/CN2010/070519, filed on Feb. 4, 2010, which claims priority to Chinese Patent Application No. 200910115552.9, filed on Apr. 24, 2009.

BACKGROUND OF THE INVENTION

The present invention relates to an injection preparation, and more particularly, to a tacrolimus injection preparation having immunosuppressive activity.

FIELD OF THE INVENTION

I. Background of Tacrolimus Pharmaceutical Preparation

Tacrolimus, as described herein, has a chemical name [3S—[3R*[E(1S*,3S*,4S*)],4S*,5R*,8S*,9E,12R*,14R*, 15S*,16R*,18S*,19S*,26aR*]]-5,6,8,11,12,13,14,15,16,17, 18,19,24,25,26a-hexa-decahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxazacyclotricosene-1,7,20,21 (4H,23H)-tetrone, monohydrate. Tacrolimus is also referred to as FK-506 in some related foreign literatures and patents, and is a common name approved by Chinese Food and Drug Administration.

Tacrolimus is a fungal metabolite extracted by Fujisawa Pharmaceutical Co., Ltd in 1982. Due to the immunosuppressive activity, tacrolimus injection and capsule are potent immunosuppressants, and useful in prevention of rejection after organ transplantation. At a molecular level, the immunosuppressive effect of tacrolimus is mediated by the cytoplasmic protein FKBP12 binding thereto. FKBP12 enables tacrolimus to enter a cell, and forms a complex with tacrolimus, which competitively specifically binds and inhibits calmodulin mediating calcium-dependent inhibitory signal delivering system in T cells, and thus prevents a series of lymphokine genes from transcription. Tacrolimus inhibits the formation of cytotoxic lymphocytes which are mainly responsible for transplant rejection, T cell activation, and TH cell-dependent B cell proliferation, as well as the generation of lymphokine such as interleukin 2, interleukin 3, and β-interferon, and the expression of the interleukin-2 receptor. In vivo study demonstrates that tacrolimus injection and capsule are efficacious in liver and kidney transplantation.

Pharmaceutical preparations available in the market which have tacrolimus as an active ingredient include injections, capsules, and ointments. Tacrolimus injection and capsule are useful in prevention of transplant rejection after liver or kidney transplantation and treatment of transplant rejection unable to be controlled by other immunosuppressive drugs after liver or kidney transplantation. Tacrolimus ointment is useful as a short-term or intermittent long-term therapy for patients with moderate to serious atopic dermatitis in case that traditional therapies are unsuitable for use due to potential risk, or the patients do not respond sufficiently to the traditional therapies or cannot tolerate the traditional therapies.

II. Research and Development Background of Tacrolimus Injection

Tacrolimus injection is clinically suitable for patients that cannot accept oral administration or require a high blood level and fast action in a short time. Therefore, tacrolimus injection can still not replaced by oral preparation in clinical treatment. However, the problem needed to be overcome in preparation of tacrolimus into an injection is the insolubility. Because tacrolimus is freely soluble in organic solvents (such as methanol, ethanol, or acetone), and practically insoluble in water, the currently existing tacrolimus injections are formulated by using a non-aqueous solvent (for example, anhydrous ethanol). However, the clinically required concentration specification (5 mg tacrolimus per ml solvent) still cannot be achieved even if anhydrous ethanol with good dissolubility is used as a solvent for dissolving tacrolimus. Based on the dosing method of tacrolimus injection employed in clinic, the injection is needed to be diluted with 5% dextrose injection or 0.9% sodium chloride injection (also referred to as normal saline) before use, to give a concentration controlled to be 0.004-0.1 mg/ml. As such, in order to achieve the requirement for clinical use by the present invention, a key point of the formulation technology of tacrolimus injection is to find a suitable surfactant to enhance the solubility of tacrolimus in anhydrous ethanol, 5% dextrose injection, or normal saline.

The surfactant refers to a compound having a fixed hydrophilic and lipophilic group, which can lower the surface or interfacial tension of two immiscible materials due to the centralization of the amphiphilic group on the surface of a solid or a liquid medicine. The surfactant is initially used in pharmacy at the beginning of 18th century; however, the use in medicine is few at first and thus the progress is slow, while the use in industry is wide. Use in medicine is developed only in the recent 100 years, and especially in the recent 40 years, rapid development is achieved with the rise of the chemical synthesis industry. The surfactant is gradually increased in types, rapidly developed in 1880s to 1890s, used in pharmacy as solubilizer, emulsifier, suspending agent, anti-oxidant, osmotic agent, detergent, disinfectant and preservative, and surface tension reducer at present, and widely used in various professional disciplines in pharmacy such as new dosage form, pharmaceutical analysis, and pharmaceutical synthesis. However, because each surfactant has different physical values such as hydrophilic-lipophilic balance (HLB) and critical micelle concentration (CMC), and different features in different application fields, it is considered that selection of a suitable surfactant to prepare tacrolimus injection is very difficult.

In the tacrolimus injection developed and manufactured by Fujisawa Pharmaceutical Co., Ltd. and marketed in China, Japan, and the US, the surfactant used is polyoxyl 60 hydrogenated castor oil (referred to as HCO-60 hereinafter), and the content of HCO-60 is 200 mg per ml tacrolimus injection. The formulation information is published, but not filed for patent.

Chinese Patent (Application No. 200580038459.X) discloses a tacrolimus injection, which contains tacrolimus, polyethylene glycol 15 hydroxystearate and anhydrous ethanol.

Korean Patent No. 0177158 discloses a solution preparation, which contains tacrolimus or a pharmaceutically acceptable salt thereof, a pharmaceutically acceptable surfactant including hydrogenated castor oil polyoxyethylene ether, and a pharmaceutically acceptable non-aqueous solvent.

Korean Patent No. 0206722 discloses a solution composition, which contains tacrolimus or a pharmaceutically acceptable salt thereof, a pharmaceutically acceptable emulsifier selected from the group consisting of egg yolk lecithin, soybean lecithin, and hydrogenated castor oil polyoxyethylene ether, and a pharmaceutically acceptable oil of liquid hydrocarbons selected from the group consisting of soybean oil and sesame oil.

Korean Patent Publication No. 2001-0006070 discloses a pharmaceutical composition, which contains a water-insoluble drug and two or more surfactants, and is characterized in that at least one surfactant can dissolve other water-insoluble surfactants and the water-insoluble drug.

In the data disclosed above, the surfactant used is hydrogenated castor oil polyoxyethylene ether including HCO-60, a combination of hydrogenated castor oil polyoxyethylene ether and a natural surfactant such as egg yolk lecithin and soybean lecithin, or polyethylene glycol 15 hydroxystearate. There is still no data indicating that other surfactants are useful in the preparation of tacrolimus injection.

In pharmacy, it is recommended that ingredients having no therapeutic effect or contents thereof in a preparation formulation should be reduced to the greatest extent, while a similar or better drug quality and clinical efficacy are achieved. The addition of any ingredients having no therapeutic effect or the increase of the amounts thereof will cause safety problems to clinical use. Therefore, in view of the analysis from pharmacy perspective, the inventions in the data published above that mostly employ the combination of multiple surfactants are not desirable. There is no related research data about the therapeutic effect and safety in clinical use, and thus the safety is debatable. The tacrolimus injection developed by Fujisawa Pharmaceutical Co., Ltd and the tacrolimus injection disclosed in Chinese Patent (Application No. 200580038459.X) employ only one surfactant, and achieve good drug quality in light of pharmaceutical quality research.

Comparative data provided in Chinese Patent (Application No. 200580038459.X) Publication Specification shows that after the tacrolimus injection with 1 ml anhydrous ethanol containing 300 mg polyethylene glycol 15 hydroxystearate and the tacrolimus injection with 1 ml anhydrous ethanol containing 200 mg HCO-60 are stored for over 7 days at room temperature, and stored for over 7 days at room temperature after 100 folds of dilution with normal saline solution, no precipitate is observed, suggesting that the use of the above two surfactants can enable the prepared tacrolimus injection to have good stability.

The data published by Fujisawa Pharmaceutical Co., Ltd and in Chinese Patent (Application No. 200580038459.X) shows that the most preferred solution formulation for tacrolimus injection is to dissolve 5 mg tacrolimus in 1 ml anhydrous ethanol, in which the surfactant is 200 mg HCO-60 or 300 mg polyethylene glycol 15 hydroxystearate. In order to find a much better surfactant, such that a similar or better tacrolimus injection quality can be achieved with a lower amount of surfactant, extensive researches are carried out by inventors of the present invention. The present invention provides an injection preparation which has tacrolimus as an active ingredient, and solves the technical problem by using polyoxylethylene castor oil ether (35).

SUMMARY OF THE INVENTION

The present invention is directed to a tacrolimus injection preparation, in which polyoxylethylene castor oil ether (35) is used as a surfactant such that water-insoluble tacrolimus is fully dissolved in a non-aqueous solvent and achieves the requirement for use, and the amount of the surfactant added is greatly reduced, thereby alleviating the safety problem of clinical use caused by inactive ingredients.

The present invention is implemented by employing the following technical solution. A tacrolimus injection preparation is provided, which contains tacrolimus, polyoxylethylene castor oil ether (35), and a non-aqueous solvent.

The technical solution may be specifically that the non-aqueous solvent is anhydrous ethanol, and a weight ratio of polyoxylethylene castor oil ether (35) to tacrolimus in the injection preparation is 10-20:1.

Polyoxylethylene castor oil ether (35), as described herein, is a substance produced by reacting castor oil and ethylene oxide at a molar ratio of 1:35 and having a main ingredient glycerol-polyethylene glycol ricinoleate, which is a pale yellow oily liquid at 26° C. or above, very soluble in dichloromethane, freely soluble in water or ethanol, and soluble in ethyl acetate. It is also referred to as polyoxyethylene ricinoleate (35), polyoxyethylene 35 castor oil, polyoxyethylene ether castor oil (35), or EL-35 for short in some related data. Because water-insoluble tacrolimus is required to be dissolved by using a non-aqueous solvent, clinically and pharmaceutically acceptable dose of any non-aqueous solvent can be used to dissolve tacrolimus and polyoxylethylene castor oil ether (35) in the present invention, in which the non-aqueous solvent is suitable for intravenous injection of human body after being diluted with normal saline or a dextrose solution. The non-aqueous solvent is preferably anhydrous ethanol. If necessary, on the basis of the ingredients described herein, other pharmaceutically acceptable additives may be added to the tacrolimus injection of the present invention as desired, including other available surfactants disclosed.

Compared with the prior art, the present invention has the following advantages. In the tacrolimus injection preparation of the present invention, only one surfactant is needed, and the addition amount of the surfactant is much lower than that of other surfactants disclosed for use in tacrolimus injection. Therefore, the present invention provides a tacrolimus injection with minimum additives, so that the clinical safety risk caused by large amount of additives is significantly lowered. In addition, a weight ratio of polyoxylethylene castor oil ether (35) to tacrolimus in the injection preparation is 10-20:1, and the tacrolimus injection prepared at this ratio generates no precipitate when being diluted with dextrose injection or normal saline, and thus has good stability.

DETAILED DESCRIPTION OF THE INVENTION

The present invention is described with reference to examples below. However, it should be understood that the examples are not intended to limit the scope specifically defined by claims of the present invention.

Comparative Example 1

Tacrolimus Injection Using Polyoxyl 60 Hydrogenated Castor Oil 5 mg tacrolimus and 200 mg polyoxyl 60 hydrogenated castor oil were dissolved in 1 ml anhydrous ethanol, then filtered through a 0.22 μm filter, and prepared into an injectable form.

Example 1

Tacrolimus Injection Using Polyoxylethylene Castor Oil Ether (35)

5 mg tacrolimus and 50 mg polyoxylethylene castor oil ether (35) (Cremophor® EL Castor Oil, BASF Company) were dissolved in 1 ml anhydrous ethanol, then filtered through a 0.22 μm filter, and prepared into an injectable form.

Example 2

Tacrolimus Injection Using Polyoxylethylene Castor Oil Ether (35)

5 mg tacrolimus and 75 mg polyoxylethylene castor oil ether (35) (Cremophor® EL Castor Oil, BASF Company) were dissolved in 1 ml anhydrous ethanol, then filtered through a 0.22 μm filter, and prepared into an injectable form.

Example 3

Tacrolimus Injection Using Polyoxylethylene Castor Oil Ether (35)

5 mg tacrolimus and 100 mg polyoxylethylene castor oil ether (35) (Cremophor® EL Castor Oil, BASF Company) were dissolved in 1 ml anhydrous ethanol, then filtered through a 0.22 μm filter, and prepared into an injectable form.

Experiment 1 and Results

Compatibility experiments of the tacrolimus solution preparations obtained in Comparative Example 1 and Examples 1-3 were conducted respectively with 5% dextrose injection and 0.9% sodium chloride injection. The solutions diluted with dextrose injection and sodium chloride injection were stored at room temperature for 24 hrs, to observe the change in stability and content of the compatible solution. The results are shown in Table 1.

TABLE 1

Change in indicated content of tacrolimus solution

| Compatible solution | Time (h) | Indicated drug content of tacrolimus solution (%) | | | |
|---|---|---|---|---|---|
| | | Comparative Example 1 | Example 1 | Example 2 | Example 3 |
| 5% dextrose injection | 0 | 98.8 | 101.7 | 100.5 | 101.9 |
| | 2 | 98.8 | 99.5 | 101.2 | 101.7 |
| | 4 | 97.7 | 99.3 | 99.8 | 100.8 |
| | 6 | 97.3 | 98.4 | 100.7 | 98.8 |
| | 10 | 97.1 | 98.4 | 98.7 | 99.1 |
| | 14 | 97.0 | 98.9 | 99.2 | 99.8 |
| | 18 | 96.8 | 99.0 | 100.4 | 99.6 |
| | 24 | 97.0 | 100.1 | 98.8 | 100.6 |
| 0.9% sodium chloride injection | 0 | 100.7 | 100.4 | 99.8 | 101.8 |
| | 2 | 99.5 | 98.1 | 98.5 | 99.8 |
| | 4 | 98.6 | 97.7 | 100.4 | 100.5 |
| | 6 | 90.4 | 98.7 | 99.2 | 100.3 |
| | 10 | 92.2 | 99.8 | 98.6 | 100.7 |
| | 14 | 90.1 | 98.9 | 101.5 | 101.5 |
| | 18 | 87.8 | 99.1 | 99.1 | 101.2 |
| | 24 | 91.5 | 100.3 | 98.3 | 98.9 |

It can be seen from Table 1 that, after the tacrolimus solution preparations obtained in Comparative Example 1 and Examples 1-3 are diluted 50 folds respectively with dextrose injection and normal saline and stored at room temperature for over 24 hrs, the tacrolimus drug contents are still stable, and no crystallization is observed. In addition, in test of 50-fold dilution of tacrolimus solution preparation obtained in Comparative Example 1 with 5% dextrose injection or normal saline solution, it can be observed that the content of the diluted solution slightly decreases after being stored at room temperature for 15 hrs. In contrast, no decrease is observed with Examples 1-3. Therefore, the tacrolimus injections provided in the present invention have a much better stability.

Experiment 2 and Results

Tacrolimus solution prepared in Example 3 was diluted with 0.9% sodium chloride injection to obtain a test solution at a concentration of 0.1 mg/ml, which was then used in irritation, hypersensitivity and hemolysis tests in animals. Vascular irritation, hypersensitivity, and hemolysis of the solution administrated by intravenous injection were observed.

1. Vascular Irritation Test in Animals 8 healthy big-ear white rabbits weighed 2.5-3.0 kg were divided into 2 groups of 4 animals each at random. The animals in the treatment group were slowly administrated with 0.1 mg/mL the diluted tacrolimus solution prepared in Example 3 by injection at the ear edge vein at a dose of 1 mL/kg animal. The solution was maintained to flow or reside in the dosed vessel for about 3 min. The animals in the control group were injected with equal amount of 0.9% sodium chloride injection at the same speed. The animals were dosed once daily for 5 days. During the administration, the formation of thrombus with local vessel dosed and the inflammatory response of surrounding tissues such as red, swelling and bleeding were visually observed with naked eyes. The animals were sacrificed at 24 hrs after the last administration, ear tissue was removed rapidly (at 3 cm from the administrated local towards the heart), fixed in 10% Formalin, embedded in paraffin, and subjected to routine section preparation and HE staining, and the morphological changes of blood vessels and surrounding tissues were observed under an optical microscope.

The results are listed in Table 2 and show that during the administration, no obvious local red, swelling, bleeding, and other symptoms caused by injection at the ear edge vein of rabbits in each group are observed with naked eyes. No obvious difference is observed between the treatment group and the control group.

TABLE 2

Visual observation and recording of vascular irritation test

| | | D1 | | D2 | | D3 | | D4 | | D5 | |
|---|---|---|---|---|---|---|---|---|---|---|---|
| Group | Rabbit No. | Thrombus | Inflammation | Thrombus | Inflammation | Thrombus | Inflammation | Thrombus | Inflammation | Thrombus | Inflammation |
| Treatment group | 1 | − | − | − | − | − | − | − | − | − | − |
| | 2 | − | − | − | − | − | − | − | − | − | − |
| | 3 | − | − | − | − | − | − | − | − | − | − |
| | 4 | − | − | − | − | − | − | − | − | − | − |
| Control group | 1 | − | − | − | − | − | − | − | − | − | − |
| | 2 | − | − | − | − | − | − | − | − | − | − |
| | 3 | − | − | − | − | − | − | − | − | − | − |
| | 4 | − | − | − | − | − | − | − | − | − | − |

Note:
no thrombus: (−), small thrombus: 1-4 mm (+), moderate thrombus: 5-14 mm (++), and large thrombus: 15 mm or larger (+++); and no inflammation change: (−), mild inflammation range: 3 cm (+), moderate inflammation range: 1/3 earconch (++), and intense inflammation range: 1/2 ear conch to whole ear (+++).

Histological observation: Vessel wall of the ear edge vein of rabbits in the treatment group is intact and smooth. No endothelial injury, thrombosis, surrounding tissue edema, inflammatory cell infiltration, inflammation, necrosis and other pathological changes are observed. There is no obvious difference between the treatment group and the control group.

2. Hypersensitivity Test in Animals 18 healthy guinea pigs weighed 250-350 g were divided into 3 groups (a test group, a negative control group, and a positive control group) of 6 animals each at random. The animals were sensitized for 3 consecutive times, by intraperitoneally injecting 0.1 mg/mL the diluted tacrolimus solution prepared in Example 3 (test group), 0.9% sodium chloride injection (negative control group), and 10% ovalbumin solution (positive control group) at a dose of 0.5 mL/animal every other day respectively. Then, the test group, the negative control group, and the positive control group were respectively divided into two groups of 3 animals each, and the animals were boosted by intravenously injecting the test sample solution, 0.9% sodium chloride injection, and 10% ovalbumin solution at a dose of 1 ml/animal respectively at days 14 and 21 after the first injection. In 15 min after the injection, the hypersensitive responses of the injected guinea pigs were observed. A positive response was determined if two or more of piloerection, dyspnea, or 3 cough sounds, or one of twitch, collapse or death appeared. Negative control group should have no hypersensitive response while all guinea pigs injected with 10% ovalbumin solution had hypersensitive responses, and death should occur to 4 or more of the 6 guinea pigs.

The results are listed in Table 3 and show that in 15 min after two times of intravenous administration of the negative control and the diluted tacrolimus solution prepared in Example 3, no hypersensitive response occurs to the 6 guinea pigs in each group, while in 1 min after two times of intravenous administration of the positive control, cough, respiratory depression, and twitch to death occur to all of the 6 guinea pigs.

TABLE 3

Hypersensitivity test results (n = 6)

| Group | Sensitizer dose | Booster dose | Occurrence of hypersensitive response |
|---|---|---|---|
| Negative control | 0.5 mL/animal | 1 mL/animal | 0/6 |
| Test group | 0.5 mL/animal | 1 mL/animal | 0/6 |
| Positive control | 0.1 mL/animal | 0.2 mL/animal | 6/6 |

The results indicate that under the test conditions, no systemic anaphylaxis appears in the hypersensitivity test of the diluted tacrolimus solution prepared in Example 3.

3. Hemolysis Test in Animals

Preparation of 2% Red Blood Cell Suspension

Several milliliters of rabbit blood were placed in an Erlenmeyer flask containing glass beads and shaken for 10 min, to remove fibrinogen and prepare a defibrinated blood. About 10 times of normal saline was added, shaken, and centrifuged. The supernatant was removed, and the precipitated red blood cells were washed 2-3 times with normal saline, till the supernatant was not red colored. The resulting red blood cells were diluted with normal saline into a 2% suspension, which was used in the day of test after being shaken.

Test Operations

2% red blood cell suspension and normal saline were added respectively to 7 test tubes following the mixing amounts shown in Table 4, uniformly mixed, and incubated in an incubator at 37° C. for 0.5 hr. Then different volumes of 0.1 mg/mL the diluted solution were respectively added (the test tube No. 6 was a negative control tube), shaken, and incubated in an incubator at 37±0.5° C. The test tubes were initially observed once every 15 min, and after 1 hr, once every 1 hr, for consecutive 4 hrs. If the solution was transparent and red colored, it was indicative of hemolysis. If there was brownish red or reddish brown flocculent precipitate in the solution, it was indicative of hemagglutination.

TABLE 4

Mixing amounts of ingredients in hemolysis test of tacrolimus injection

| Test tube | 1 | 2 | 3 | 4 | 5 | 6 (−) | 7 (+) |
|---|---|---|---|---|---|---|---|
| 2% red blood cell suspension (ml) | 2.5 | 2.5 | 2.5 | 2.5 | 2.5 | 2.5 | 2.5 |
| Normal saline (ml) | 2.4 | 2.3 | 2.2 | 2.1 | 2.0 | 2.5 | 0 |
| Diluted tacrolimus solution prepared in Example 3 (ml) | 0.1 | 0.2 | 0.3 | 0.4 | 0.5 | 0 | 0 |
| Distilled water (ml) | 0 | 0 | 0 | 0 | 0 | 0 | 2.5 |

Test Results

Hemolysis occurs immediately after distilled water is added to the solution in test tube No. 7, while the solutions in the test tubes adding with tacrolimus solution (test tube Nos. 1-5) and the normal saline tube No. 6 do not appear transparent and red within the given time, and there is also no occurrence of brownish red or reddish brown flocculent precipitate, suggesting that the diluted tacrolimus solution prepared in Example 3 does not have hemolysis and agglutination effects. The results are shown in Table 5.

TABLE 5

Hemolysis test results

| Test tube No. | 1 | 2 | 3 | 4 | 5 | 6 (−) | 7 (+) |
|---|---|---|---|---|---|---|---|
| Incubated at 37° C. for 15 min | − | − | − | − | − | − | +++ |
| Incubated at 37° C. for 30 min | − | − | − | − | − | − | +++ |
| Incubated at 37° C. for 45 min | − | − | − | − | − | − | +++ |
| Incubated at 37° C. for 1.0 hr | − | − | − | − | − | − | +++ |
| Incubated at 37° C. for 2.0 hrs | − | − | − | − | − | − | +++ |
| Incubated at 37° C. for 3.0 hrs | − | − | − | − | − | − | +++ |
| Incubated at 37° C. for 4.0 hrs | − | − | − | − | − | − | +++ |

Note:
+++ complete hemolysis;
++ partial hemolysis;
+ agglutination;
− no hemolysis and no agglutination It can be seen from Table 5 that the diluted tacrolimus solution prepared in Example 3 does not cause hemolysis or agglutination over 4 hrs.

What is claimed is:

1. A tacrolimus injection preparation, characterized in that the injection preparation comprises tacrolimus, polyoxyethylene castor oil ether (35), and a nonaqueous solvent; wherein the weight ratio of polyoxylethylene castor oil ether (35) to tacrolimus in the injection preparation is about 10-20:1 and the injection preparation is storage stable when being diluted in a dextrose or saline solution.

2. The tacrolimus injection preparation according to claim 1, characterized in that the non-aqueous solvent is anhydrous ethanol.

3. The tacrolimus injection preparation according to claim 1, wherein the weight ratio of polyoxylethylene castor oil ether (35) to tacrolimus in the injection preparation is preferably about 10-15:1.

* * * * *